United States Patent [19]

Barri et al.

[11] Patent Number: 5,342,596
[45] Date of Patent: Aug. 30, 1994

[54] PROCESS FOR MAKING THETA-1 ZEOLITE

[75] Inventors: Sami A. I. Barri, London; Philip Howard, St. Margarets Twickenham; Clive D. Telford, Ascot, all of United Kingdom

[73] Assignee: The British Petroleum Company Limited, London, United Kingdom

[21] Appl. No.: 335,557

[22] Filed: Dec. 29, 1981

[30] Foreign Application Priority Data

Jan. 8, 1981 [GB] United Kingdom ............ 81C0532

[51] Int. Cl.$^5$ .......................................... C01B 33/34
[52] U.S. Cl. ................................. 423/710; 423/718; 502/77
[58] Field of Search ................. 423/328–330; 252/455; 260/448 C; 208/120; 502/77

[56] References Cited

U.S. PATENT DOCUMENTS

| | | | |
|---|---|---|---|
| 4,086,186 | 4/1978 | Rubin et al. | 423/328 |
| 4,242,233 | 12/1980 | Ball et al. | 260/448 C |
| 4,377,502 | 3/1983 | Klotz | 423/328 X |
| 4,407,728 | 10/1983 | Ball et al. | 423/329 |
| 4,478,806 | 10/1984 | Ball et al. | 423/328 |

FOREIGN PATENT DOCUMENTS

| | | |
|---|---|---|
| 0055045 | 6/1982 | European Pat. Off. |
| 0065400 | 11/1982 | European Pat. Off. |
| 1365318 | 8/1974 | United Kingdom ............ 423/329 |

OTHER PUBLICATIONS

Aiello et al. "J. Chem. Soc. (A)" 1970, pp. 1470–1475.
Whyte et al. "Journal of Catalyst" 1971 20, pp. 88–96.

*Primary Examiner*—Asok Pal
*Attorney, Agent, or Firm*—Brooks Haidt Haffner & Delahunty

[57] ABSTRACT

Novel crystalline alumino silicates having the following composition in terms of the mole ratio of the oxides:

$$0.9\pm0.2\ M_{2/n}:Al_2O_3:x\ SiO_2:yH_2O$$

wherein M is at least one cation having a valence n, x is at least 10 and y/x is between 0 and 25, said aluminosilicates having a characteristic X-ray diffraction pattern. The cation M in the aluminosilicates is preferably selected from H$^+$, ammonium, alkali metal cations, alkaline earth metal cations, organic nitrogencontaining cations, aluminum cations, gallium cations and mixtures thereof. The invention also comprises a process for producing the aluminosilicate by mixing together a source of silica, a source of alumina, a source of alkali metal(s), water and diethanolamine until a homogeneous gel is formed and crystallizing the mixture at a temperature above 70° C. for a period of at least 2 hours.

5 Claims, No Drawings

PROCESS FOR MAKING THETA-1 ZEOLITE

The present invention relates to novel silicates and to methods of preparing the same. More particularly, this invention relates to novel crystalline aluminosilicates having catalytic properties, to methods for preparing the same, and hydrocarbon conversion therewith.

Aluminosilicates, both natural and synthetic, have generally been known as zeolites. Zeolitic materials, both natural and synthetic, have been demonstrated to have catalytic properties for various types of hydrocarbon conversion. Certain zeolitic materials are ordered porous crystalline aluminosilicates having a definite crystalline structure within which there are a large number of small cavities which are interconnected by a number of smaller channels. These cavities and channels are uniform in size, and are capable of adsorbing molecules of certain dimensions while rejecting those of larger dimensions. These materials have therefore been used as molecular sieves and include a wide variety of positive ion-containing crystalline aluminosilicates, both natural and synthetic. Such aluminosilicates have been described as having a rigid three-dimensional network of $SiO_4$ and $AlO_4$ in which the tetrahedra are cross-linked by the sharing of oxygen atoms whereby the ratio of the total aluminium and silicon atoms to oxygen is 1:2. The electrovalence of the aluminium-containing tetrahedra is balanced by the inclusion in the crystal of a cation, for example, an alkali metal or an alkaline earth metal cation. This can be expressed by a formula in which the ratio of Al to the umber of the various cations, such as Ca/2, Sr/2, Na, K or Li, is equal to unity. One type of cation can be exchanged in entirety or partially by another type of cation utilizing ion exchange techniques in a conventional manner. By means of such cation exchange, it is possible to vary the size of the pores in the given aluminosilicate. The spaces between the tetrahedra may be occupied by molecules of water in the uncalcined form of the zeolite. More recently, the structure of those zeolites has been characterised by their X-ray diffraction patterns. A list of the various types of zeolites as characterised by their X-ray diffraction pattern can be found in the book by Meier, W. M. and Olson, D. H. entitled, "Atlas of Zeolite Structure Types", published by the Structure Commission of the International Zeolite Association (1978) and distributed by Polycrystal Book Service, Pittsburgh, Pa. USA.

Our copending European application publication No. 2900 describes a process for preparing a crystalline aluminosilicate having an X-ray diffraction pattern substantially the same as that of ZSM-5 by crystallising a mixture containing a source of silica, a source of alumina, a source of alkali metal and a nitrogenous organic base which is a di- or tri- alkanolamine.

It has now been found that a novel crystalline aluminosilicate, designated Theta-1, can be produced by crystallisation from a mixture containing a source of silica, a source of alumina, a source of alkali metal(s), water and an organic nitrogen containing base, such as diethanolamine.

Accordingly, the present invention provides novel crystalline aluminosilicates having the following composition in terms of the mole ratios of the oxides:

$$0.9 \pm 0.2\ M_{2/n}O : Al_2O_3 : xSiO_2 : yH_2O$$

wherein M is at least one cation having a valence n, x is at least 10 and y/x is between 0 to 25, wherein the aluminosilicate in the calcined hydrogen-form has an X-ray diffraction pattern substantially as set forth in Table A of the specification.

Preferably the aluminosilicate in the calcined hydrogen-form has an X-ray diffraction pattern substantially as set forth in Table B of the specification.

By the "calcined hydrogen-form" is meant throughout this specification the aluminosilicate in the calcined state and wherein the cation M is hydrogen.

The cation M in the zeolite may be selected from $H^+$, ammonium, alkali metal cations, alkaline earth metal cations, organic nitrogen containing cations, aluminium cations, gallium cation and mixtures thereof.

The cations present in the aluminosilicate may be replaced using conventional ion exchange techniques either wholly or partially by other cations e.g. hydrogen ions or metal cations.

The calcined hydrogen-form of the aluminosilicate zeolite may be produced by known methods such as exchange with acidic or ammonium cations or a combination of the two followed by one or more calcination stages.

The aluminosilicates according to the present invention, designated herein as "Theta-1" aluminosilicates, have an X-ray diffraction pattern shown in Table A below.

The specific values in the Tables were determined using copper K-alpha radiation and a computer step scan.

The peak heights, I, and their position as a function of 2 theta, where theta is the Bragg angle, were read from the spectrometer output. From this output the relative intensities $100 \times I/I_o$, where $I_o$ is the intensity of the strongest peak, and d the interplanar spacing in Å, corresponding to the recorded peaks were calculated.

It will be understood by those skilled in the art that the X-ray diffraction pattern of aluminosilicates may vary in the values of $I/I_o$ and the d-spacing depending for example upon whether the sample being examined is calcined or uncalcined, upon the temperature of calcination, upon the nature of the cation present in the aluminosilicate, the mole ratio of silica to alumina, and the particle size of the aluminosilicate.

The aluminosilicate is suitably produced from an initial mixture containing a source of silica, a source of alumina, a source of alkali metal(s), water and an organic nitrogen containing base.

The silica to alumina mole ratio in the initial mixture may suitably be at least 10:1. Preferably the silica to alumina mole ratio and the free alkali metal(s) hydroxide to water mole ratio, defined as:

[(Number of moles of total alkali metal(s)) −
(Number of moles of alkali metal(s) required
to convert alumina present to alkali metal
aluminate(s), ie $MAlO_2$)]
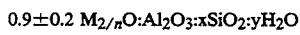
Number of moles of water present are greater than 40:1 and greater than $2 \times 10^{-3}:1$ respectively. Even more preferably the silica to alumina mole ratio is in the range 60:1 to 500:1 and the free alkali metal(s) hydroxide to water mole ratio is in the range $2 \times 10^{-3}:1$ to $8 \times 10^{-3}:1$. Similarly the mole ratio of silica to free alkali metal(s) hydroxide may suitably be in the range 1:1 to 20:1, preferably between 5:1 and 15:1, and the mole ratio of water to silica may suitably be in the range 4:1 to 50:1, preferably in the range 6:1 to 30:1, even more preferably in the range 9:1 to 30:1.

Using diethanolamine as the nitrogen containing organic base, Theta-1 substantially free from other crystalline aluminosilicates, e.g. ZSM-5, can be produced at a silica to alumina mole ratio greater than 60:1 and a free alkali metal(s) hydroxide to water ratio less than $8 \times 10^{-3}:1$ in the initial mixture. At a silica to alumina mole ratio in the range 40:1 to 60:1 and a free alkali metal(s) hydroxide to water ratio less than $8 \times 10^{-3}:1$ in the initial mixture or at silica to alumina mole ratios in the range 60:1 to 150:1 and a free alkali metal(s) hydroxide to water ratio in the initial mixture greater than $8 \times 10^{-3}:1$, Theta-1 admixed with for example ZSM-5 may be produced.

The aluminosilicate, Theta-1, is suitably prepared by forming a mixture of all the reactants, by simply mixing them together while maintaining the mixture suitably at a temperature between 0° to 100° C., preferably between 20° and 60° C., until a homogeneous gel is formed and crystallising the mixture so-formed at a temperature above 70° C., preferably between 100° and 220° C. for a period of at least 2 hours, preferably for 6 to 240 hours. The optimum crystallisation period can vary and may depend upon such factors as the temperature, pH and gel composition. Preferably the source of silica is an amorphous silica sol which is diluted with water. It is preferred that the silica source is added to the other reagents in such a way as to commence gelation at a relatively high pH.

The product obtained in this manner contains cations which may be hydrogen, alkali metal(s), aluminium, or organic nitrogen containing cations or any combination thereof.

The cations in the product may be converted to hydrogen to give rise to the hydrogen-form of the product. This may be achieved by techniques known to those skilled in the art, e.g. (a) ammonia exchange followed by calcination, (b) acid exchange or a combination of (a) and (b).

The product or the hydrogen-form thereof may also be subjected to exchange or impregnation with a metal suitable for imparting a specific type of catalytic activity. The metal compounds which may be used for ion-exchange and/or impregnation may be compounds of any one of the following metals or groups of metals, namely those belonging to Groups IB, IIB, IIIA, IVA, VA, VIB, VIIB and VIII according to the Periodic Table due to Mendeleef. Specifically, compounds of copper, silver, zinc, aluminium, gallium, indium, thallium, lead, antimony, bismuth, chromium, molybdenum, tungsten, manganese, iron, cobalt, nickel, ruthenium, rhodium, palladium, iridium, platinum and rhenium are preferred.

The aluminosilicate products of the present invention may be bound in a suitable binding material before or after impregnation or after exchange with one of the aforementioned metal compounds to produce an attrition resistant catalyst. The binder for this purpose may be any one of the conventional alumina or silica binders.

The aluminosilicates of the present invention may be used, whether or not impregnated and/or ion-exchanged, as catalysts for any of the following reactions. Alkylation, dealkylation, dehydrocyclodimerisation, aromatisation, transalkylation, isomerisation, dehydrogenation, hydrogenation, cracking, cyclisation, oligomerisation, polymerisation, and dehydration reactions, the last named in particular with reference to dehydration of alcohols and ethers. The aluminosilicate Theta-1 may be used as such or as a component of a catalysts mixture containing other active or inactive components. The Theta-1 may be used in admixture with other zeolites. The catalysts may be used in the form of fixed, fluidised or moving beds.

TABLE A

| 2 theta | d-spacing | Relative intensity $100 \times I/I_o$ |
|---|---|---|
| 8.15 ± 0.5 | 11.5 — 10.2 | 50 to 100 |
| 10.16 ± 0.5 | 8.29 — 9.14 | 5 to 25 |
| 12.77 ± 0.5 | 7.20 — 6.66 | 10 to 20 |
| 16.36 ± 0.5 | 5.58 — 5.25 | 5 to 15 |
| 19.42 ± 0.5 | 4.68 — 4.45 | 5 to 15 |
| 20.35 ± 0.5 | 4.47 — 4.26 | 50 to 100 |
| 24.22 ± 0.5 | 3.75 — 3.60 | 50 to 100 |
| 24.65 ± 0.5 | 3.68 — 3.54 | 30 to 90 |
| 25.75 ± 0.5 | 3.52 — 3.39 | 15 to 45 |
| 35.63 ± 0.5 | 2.55 — 2.48 | 15 to 40 |
| scanned up to $2\theta = 36$ | | |

TABLE B

| 2 theta | d-spacing | Relative intensity $100 \times I/I_o$ Preferred |
|---|---|---|
| 8.15 ± 0.5 | 11.5 — 10.2 | 60 to 100 |
| 10.16 ± 0.5 | 8.29 — 9.14 | 10 to 20 |
| 12.77 ± 0.5 | 7.20 — 6.66 | 12 to 18 |
| 16.36 ± 0.5 | 5.58 — 5.25 | 7 to 11 |
| 19.42 ± 0.5 | 4.68 — 4.45 | 9 to 12 |
| 20.35 ± 0.5 | 4.47 — 4.26 | 60 to 100 |
| 24.22 ± 0.5 | 3.75 — 3.60 | 60 to 100 |
| 24.65 ± 0.5 | 3.68 — 3.54 | 40 to 90 |
| 25.75 ± 0.5 | 3.52 — 3.39 | 20 to 40 |
| 35.63 ± 0.5 | 2.55 — 2.48 | 15 to 30 |
| scanned up to $2\theta = 36$ | | |

TABLE 1

| 2 Theta | d-spacing | $100 \times I/I_o$ |
|---|---|---|
| 8.15 | 10.85 | 100 |
| 10.16 | 8.71 | 16 |
| 12.77 | 6.93 | 16 |
| 16.36 | 5.42 | 10 |
| 19.42 | 4.57 | 10 |
| 20.35 | 4.36 | 77 |
| 24.22 | 3.70 | 74 |
| 24.65 | 3.61 | 49 |
| 25.75 | 3.46 | 23 |
| 35.63 | 2.52 | 22 |

Theta-1, the aluminosilicate of this invention has a framework density, $d_f$, of 20.5±0.3 TO$_4$ units per 1000 Angstrom$^3$. Theta-1 belongs to a class of materials having a framework structure consisting of a rigid, regular three dimensional network of tetrahedral units represented as TO$_4$, where T may be a Si atom or an Al atom. The network is formed by the cross-linking through the oxygen atoms of the TO$_4$ units. Framework density is the number of such TO$_4$ units per 1000 Angstrom$^3$ of a zeolite crystal.

Theta-1 has a sorption characteristic (i.e. amount of fluid retained by the zeolite, whether by absorption or adsorption, within the accessible void volumes of the zeolite structure at a given temperature under equilibrium condition as shown in the following Table 2.

TABLE 2

| Sorbate | Kinetic Diameter (Å) | Equilibrium Sorption at 25° C. for Theta-1 | |
|---|---|---|---|
| | | (wt %) | (ml/100 g) |
| n-Hexane | 4.3 | 6.8 | 10.3 |
| p-xylene | 5.85 | 8.0 | 9.2 |
| m-xylene | 6.0 | 6.1 | 7.0 |

The present invention is further illustrated with reference to the following Examples.

EXAMPLE 1

A solution was prepared from a mixture of sodium aluminate (2.09 g), sodium hydroxide (1.68 g) and water (20 ml).

Diethanolamine (9.95 g) was melted and added to the solution and the resultant solution ("A") was stirred and maintained at 30° C. for 10 minutes with constant stirring.

66 g of a commercial silica gel, 'Ludox AS40' (Reg. Trade Mark) which contains 40% by weight of silica, was diluted with 40 ml of water to form solution "B". Thereafter solution "B" was added dropwise to solution "A" over a period of 40 minutes with constant stirring. Stirring was continued for a further 20 minutes and then the resultant gel was transferred to an oven and crystallised at 170° C. for 93 hours in a revolving stainless steel pressure vessel.

The product was removed and found to contain substantially Thetal with a trace of MFI type zeolites (as defined in the "Atlas of Zeolite Structure Types" referred to above) and a little uncrystallised material, and it had in the calcined hydrogen form an X-ray diffraction pattern as shown in Table 1 above. On calcination it was shown to contain Si (40.6% w/w), Al (1.34% w/w) and Na (0.87% w/w).

EXAMPLE 2

A solution was prepared from a mixture of sodium aluminate (2.41 g), and potassium hydroxide (1.43 g) in water (20 ml).

Diethanolamine (13.8 g) was melted and added to the solution and the resultant solution "C" was stirred for 10 minutes at 30° C.

A solution "D", consisting of 74.9 g of Ludox AS 40 and 44 ml of water was added dropwise to solution C, whilst stirring and maintaining constant temperature (30° C.). Addition of solution D was complete after 2 hours and the gel product was charged to a revolving pressure vessel and crystallised at 170° C. for 140 hours. The product was washed and dried and calcined as described in Example 1. It was found by X-ray diffraction, to be substantially Theta-1 with a little crystobalite. The X-ray diffraction pattern corresponded to an aluminosilicate in accordance with the present invention. It contained Si (43.7% w/w), Al (2.4% w/w), Na (0.28% w/w) and K (1.48% w/w).

EXAMPLE 3

A solution was prepared from a mixture of sodium aluminate (2.7 g) and lithium hydroxide monohydrate (1.40 g) in water (28 g).

Diethanolamine (35 g) was melted and added to the solution and the resultant solution "E" was stirred for circa 5 minutes at circa 30° C.

A solution "F" consisting of 99 g Ludox AS 40 and 71 g water, was added to solution E over a period of approximately 20 minutes while stirring thoroughly and maintaining constant temperature (30° C.). The resultant gel was stirred at 30° C. for a further 30 minutes. The gel was charged to a revolving pressure vessel and crystallised at 175° C. for 48 hours. The product was washed and dried. It was found by X-ray diffraction to contain Theta-1 (ca 30%), having an X-ray diffraction pattern corresponding to an aluminosilicate in accordance with the present invention. It contained Si (31.4% w/w), Al (1.1% w/w), Na (0.7% w/w) and Li (0.23% w/w).

EXAMPLE 4

The procedure of Example 3 was followed except solution E was replaced by solution "G" consisting of 3 g sodium aluminate, 30 ml 0.57N aqueous rubidium hydroxide and 40 g melted diethanolamine; solution F was replaced by solution "H" consisting of 107 g of Ludox AS 40 and 76 g of water; and the resultant gel crystallised for 72 hours. The washed and dried product was shown by X-ray diffraction to contain Theta-1 (ca 50%) and a minor amount of crystobalite and it had an X-ray diffraction pattern corresponding to an aluminosilicate in accordance with the present invention. It contained Si (26.4% w/w), Al (0.95% w/w), Na (0.42% w/w) and Rb (0.3% w/w).

EXAMPLE 5

Potassium hydroxide (5.7 g) was dissolved in water (40 g) which was then heated to 80° C. Aluminium isopropoxide (9.4 g) was added slowly while maintaining constant temperature (80° C.). The resultant solution was cooled to 30° C.

Diethanolamine (41 g) was melted and added to the solution and the resultant solution "I" was stirred for circa 5 minutes at 30° C.

A solution "K" of Ludox (163 g) and water (200 g) was added to solution I over a period of circa 20 minutes while stirring thoroughly at circa 30° C. The resultant gel was stirred for a further 30 minutes at 30° C. The gel was charged to a revolving pressure vessel and crystallised at 175° C. for 160 hours. The resultant product was washed and dried. It was found by X-ray diffraction to contain Theta-1 (circa 50%) and a trace of crystobalite. It had an X-ray diffraction pattern corresponding to an aluminosilicate in accordance with the present invention and it contained Si (30.7% w/w), Al (1.35% w/w), and K (2.32% w/w).

EXAMPLE 6

The procedure of Example 3 was followed except solution E was replaced by solution "L" consisting of 6.65 g sodium hydroxide, 10.3 g sodium aluminate, 140 g water and 180 g melted diethanolamine; solution F was replaced by solution "M" consisting of 500 g of Ludox AS 40 and 355 g of water; and the resultant gel crystallised for 24 hours. The washed and dried product was found by X-ray diffraction to contain substantially pure Theta-1. It contained Si (35.0% w/w), Al (0.91% w/w), and Na (0.36% w/w), and had an X-ray diffraction pattern corresponding to an aluminosilicate in accordance with the present invention.

EXAMPLE 7

The procedure of Example 3 was followed except solution E was replaced by solution "N" consisting of 1.80 g potassium hydroxide, 1.0 g sodium aluminate, 0.23 g sodium hydroxide, 50 g water and 14 g melted diethanolamine; and solution F was replaced by solution "P" consisting of 68 g of Ludox AS 40 and 95 g of water. The washed and dried product was found by X-ray diffraction to contain Theta-1 (ca 50%). It

EXAMPLE 8

The procedure of Example 6 was followed except 12.6 g rather than 10.3 g of sodium aluminate was used and crystallisation was effected over 18 hours in a rocking pressure vessel. The washed and dried product was found by X-ray diffraction to contain substantially pure Theta-1. It contains Si (27% w/w), Al (0.81% w/w) and Na (0.60% w/w) and had an X-ray diffraction pattern corresponding to an aluminosilicate in accordance with the present invention.

EXAMPLE 9

A quantity of Theta-1 as produced in Example 1 was calcined at 600° C. and refluxed in molar ammonium nitrate for 4 hours. The resultant product was recalcined at 600° C. to produce the hydrogen form thereof which contained approximately Si (40.6% w/w), Al (1.34% w/w) and Na (0.06% w/w). The ammonium nitrate was in aqueous solution.

A reactor was loaded with Theta-1 (2.8 g, approx 15 mls) sieved to BSS mesh 12-13. After activation of the aluminosilicate in situ in air at 550° C., a feed of n-butane was passed (WHSV 3.1) over the activated aluminosilicate at a temperature of 550° C. and at atmospheric pressure.

The product, after 30 minutes on stream was found to contain the following by weight %.

TABLE 3

| Hydrogen | 0.9 |
|---|---|
| $C_1$–$C_3$ aliphatic | 36.0 |
| $C_4$ aliphatic | 45.0 |
| $C_4$–$C_7$ aliphatic | 2.5 |
| $C_6$–$C_8$ aromatic | 14.4 |
| >C9 aromatic ca. | 0.7 |
| | 99.5 |

EXAMPLE 10

The material tested in Example 9 was regenerated by in situ oxidation of the deposited coke. It was then refluxed in 120 ml of gallium nitrate solution containing the equivalent of 1 g of gallium metal and subsequently washed to remove excess gallium and then dried. A reactor was then loaded with the Ga/Theta-1 and the catalyst was activated in situ with air at 550° C.

A feed of n-butane was passed over the catalyst (WHSV 1.07) at a temperature of 542° C. and the product was analysed at 30 minutes and found to contain the following by weight %.

TABLE 4

| Hydrogen | 3.0 |
|---|---|
| $C_1$–$C_3$ | 39.4 |
| $C_4$ aliphatic | 23.0 |
| $C_5$–$C_7$ aliphatic | 0.40 |
| $C_6$–$C_8$ aromatic | 32.3 |

TABLE 4-continued

| >C9 aromatic | 0.7 |
|---|---|
| | 98.8 |

We claim:

1. A process for producing a crystalline aluminosilicate having the following composition in terms of the mole ratios of the oxides:

$$0.9 \pm 0.2\ M_2O_n : Al_2O_3 : xSiO_2 : yH_2O$$

wherein M is at least one cation having the valence n, x is at least 10 and y/x is between 0 and 25, said aluminosilicate in the calcined hydrogen form having an x-ray diffraction pattern substantially as set forth in Table 1 of the specification, which process comprises mixing a source of silica, a source of alumina, a source of alkali metal(s), water and diethanolamine until a homogeneous gel is formed, wherein in the mixture the silica to alumina mole ratio is greater than 40:1, the free alkali metal(s) hydroxide to water mole ratio is greater than $2 \times 10^{-3}$:1, the mole ratio of silica to alkali metal(s) oxide or hydroxide is in the range 1:1 to 20:1 and the mole ratio of water to silica is in the range of 4:1 to 50:1, and crystallising the mixture at a temperature above 70° C., for a period of at least 2 hours.

2. A process as claimed in claim 1 wherein the mixing is effected at a temperature in the range of 0° to 100° C. and the mixture is crystallised at a temperature in the range from 70° C. to 200° C.

3. A process according to claim 1 wherein in the mixture the silica to alumina mole ratio is in the range 60:1 to 500:1, the free alkali metal(s) hydroxide to water mole ratio is in the range $2 \times 20^{-3}$:1 to $8 \times 10^{-3}$:1, the mole ratio of silica to alkali metal(s) oxide or hydroxide is in the range 5:1 to 15:1 and the mole ratio of water to silica is in the range 6:1 to 30:1.

4. A process according to claim 1 wherein the aluminosilicate product or the hydrogen-form thereof is subjected to exchange or impregnation with any one of the metals or groups of metals belonging to Groups IB, IIB, IIIA, IVA, VA, VIB, VIIB and VIII according to the Periodic Table due to Mendeleef.

5. A process for producing a crystalline aluminosilicate having the following composition in terms of the mole ratios of the oxides:

$$0.9 \pm 0.2\ M_2O_n : Al_2O_3 : xSiO_2 : yH_2O$$

wherein M is at least one cation having the valence n, x is at least 10 and y/x is between 0 and 25, said aluminosilicate in the calcined hydrogen form having an x-ray diffraction pattern substantially as set forth in Table 1 of the specification, which process comprises mixing a source of silica, a source of alumina, a source of alkali metal(s), water and an diethanolamine until a homogeneous gel is formed comprising OH$^-$ ions, wherein in the mixture the silica to alumina mole ratio is greater than 40:1, and the mole ratio of silica to the OH$^-$ ions in the mixture is in the range from 5-15:1, and crystallising the mixture at a temperature above 70° C., for a period of at least 2 hours.

* * * * *

UNITED STATES PATENT AND TRADEMARK OFFICE
CERTIFICATE OF CORRECTION

PATENT NO. : 5,342,596
DATED : August 30, 1994
INVENTOR(S) : Sami A.I. Barri, et al It is certified that error appears in the above-indentified patent and that said Letters Patent is hereby corrected as shown below:

Col. 1, l. 32, correct the spelling of the word "number"

Col. 5, l. 20, change "gel" to --sol--

Column 8, line 31,

Claim 2, line 4, change "200°C" to --220°C--

Signed and Sealed this

Fourth Day of April, 1995

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,342,596
DATED : August 30, 1994
INVENTOR(S) : SAMI A.I. BARRI, PHILIP HOWARD and CLIVE D. TELFORD It is certified that error appears in the above-indentified patent and that said Letters Patent is hereby corrected as shown below:

Cols. 4 and 5, strike the passage reading from line 64 of col. 4 through col. 5, lines 1 through 8; and insert in lieu thereof:

--The adsorption properties of Theta-1 were determined on the hydrogen form of Theta-1. The data is set forth in Table 2

UNITED STATES PATENT AND TRADEMARK OFFICE
CERTIFICATE OF CORRECTION

PATENT NO. : 5,342,596
DATED : August 30, 1994
INVENTOR(S) : SAMI A.I. BARRI, PHILIP HOWARD and CLIVE D. TELFORD It is certified that error appears in the above-indentified patent and that said Letters Patent is hereby corrected as shown below:

| Table 2. Adsorption properties of Theta-1 | | | |
|---|---|---|---|
| Adsorbate | Kinetic diameter (Å) | $V_p$ ($cm^3 g^{-1}$) | $V_f$ |
| $N_2$ | 3.64 | 0.1 | 0.21 |
| $H_2O$ | 2.65 | 0.058 | 0.12 |
| n-hexane | 4.3 | 0.089 | 0.18 |
| p-xylene | 5.85 | 0.062 | 0.13 |
| Cyclohexane | 6.0 | 0.021 | 0.04 |
| m-xylene | 6.0 | 0.031 | 0.06 |

Void volume $V_p$ ($cm^3 g^{-1}$) is the total micropore volume in hydrogen form of Theta-1, calculated using normal liquid density at adsorption temperature. The void fraction, $V_f = V_p$ ($cm^3 g^{-1}$) $\times d_c$ ($g\, cm^{-3}$), where $d_c$ (=2.05 $g\, cm^{-3}$) is the measured crystal density. All samples activated by calcination at 550 °C for 1 h. Adsorption measurements by microbalance techniques at room temperature with relative pressure $P/P_0 = 0.5$. $N_2$ adsorption by single point Brunauer-Emmett-Teller test, −183 °C $P/P_0 = 0.9$.

Signed and Sealed this

Thirteenth Day of June, 1995

*Attest:*

BRUCE LEHMAN

*Attesting Officer*     *Commissioner of Patents and Trademarks*